United States Patent [19]

Kanou et al.

[11] Patent Number: 5,723,628
[45] Date of Patent: Mar. 3, 1998

[54] PROCESS FOR PREPARING CARBOXYLIC ACID DERIVATIVE

[75] Inventors: Fumihiko Kanou, Himeji; Toshihiro Takeda, Kobe; Natsuki Mori, Takasago; Kazunori Kan, Nishinomiya, all of Japan

[73] Assignee: Kanegafuchi Kagaku Kogyo Kabushiki Kaisha, Osaka, Japan

[21] Appl. No.: 693,229

[22] PCT Filed: Dec. 25, 1995

[86] PCT No.: PCT/JP95/02673

§ 371 Date: Aug. 22, 1996

§ 102(e) Date: Aug. 22, 1996

[87] PCT Pub. No.: WO96/20188

PCT Pub. Date: Jul. 4, 1996

[30] Foreign Application Priority Data

Dec. 28, 1994 [JP] Japan ................................ 6-329089

[51] Int. Cl.⁶ .......................................... C07D 333/16
[52] U.S. Cl. ............................................... 547/66
[58] Field of Search ........................................ 549/66

[56] References Cited

U.S. PATENT DOCUMENTS 4,968,814 11/1990 Blacklock et al. .
5,474,919 12/1995 Chartrain et al. .
5,574,176 11/1996 Mathre et al. .

OTHER PUBLICATIONS

Blacklock et al., Journal of Organic Chemistry, vol. 58 pp. 1672–1679, 1993.

Morrison et al., "Organic Chemistry" 5th ed., Allyn & Bacon, Inc., (1987), pp. 880–881.

Primary Examiner—José G. Dees
Assistant Examiner—Mary C Cebulak
Attorney, Agent, or Firm—Armstrong, Westerman, Hattori, McLeland & Naughton

[57] ABSTRACT

There is described a process for preparing 3-(2-thienylthio) butyric acid by converting a compound having the formula (III):

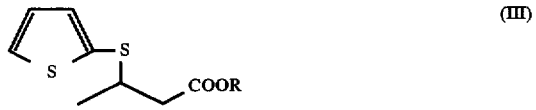

wherein R is a straight chain or branched $C_1$ to $C_4$ alkyl group, whereby the production of 3-(3-thienylthio)butyric acid as a by-product which is the position isomer can be controlled to at most 0.1 mol %. 3-(2-Thienylthio)butyric acid is a useful compound as an intermediate for a medicinal compound.

11 Claims, No Drawings

PROCESS FOR PREPARING CARBOXYLIC ACID DERIVATIVE

SPECIFICATION

This application is a 371 of PCT/JP/02673 filed Dec. 25, 1995.

TECHNICAL FIELD

The present invention relates to a process for preparing 3-(2-thienylthio)butyric acid having the structural formula (I):

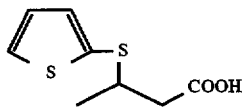

The present compound is an important key intermediate in the preparation of a medicament having the structural formula (V):

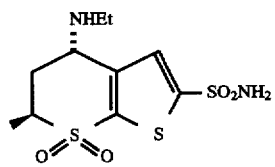

which is used in the treatment of glaucoma, MK-507 (see Fortschritte der Ophthalmologie, 88, 513 (1991)).

BACKGROUND ART

As a process for preparing 3-(2-thienylthio)butyric acid, there is known a process wherein 3-(2-thienylthio)butyric acid methyl ester is hydrolyzed with an about 6N aqueous solution of hydrochloric acid under refluxing conditions (see Journal of Organic Chemistry, 58 [7]; 1672 (1993), U.S. Pat. No. 4,968,814 and Japanese Unexamined Patent Publication No. 224576/1992).

However, in the above-mentioned process, the production of 3-(3-thienylthio)butyric acid having the structural formula (II):

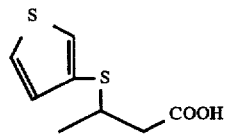

as a by-product is unavoidable. Furthermore, the removal of this by-product is extremely difficult because in the subsequent process for the synthesis of the medicament used in the treatment of glaucoma having the structural formula (V), this by-product is subjected to the chemical conversion in the same way as in 3-(2-thienylthio)butyric acid.

Therefore, in order to use the obtained 3-(2-thienylthio) butyric acid as an intermediate for a medicament, it has been desired to develop a process for preparing 3-(2-thienylthio) butyric acid wherein the content of 3-(3-thienylthio)butyric acid is controlled to at most 0.1 mol %.

DISCLOSURE OF THE INVENTION

As the result of the detailed investigation of the present inventors to control the production of 3-(3-thienylthio) butyric acid as a by-product, they have found that in a contact reaction of a compound having the formula (III):

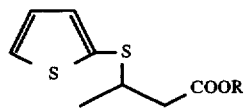

wherein R is a straight chain or branched $C_1$ to $C_4$ alkyl group, with an aqueous solution of acid, the production of 3-(3-thienylthio)butyric acid as a by-product can be dramatically controlled to at most 0.1 mol % by adding an organic solvent or an organic acid. Consequently, the present invention has been accomplished.

Namely, the present invention relates to a process for preparing a compound having the structural formula (I):

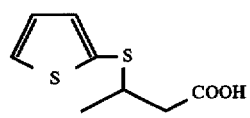

characterized by, in a reaction of a compound having the formula (III):

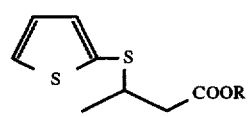

wherein R is a straight chain or branched $C_1$ to $C_4$ alkyl group, with an aqueous solution of acid, adding an organic solvent or an organic acid whereby the production of a by-product compound having the structural formula (II):

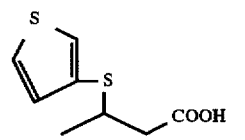

is controlled to at most 0.1 mol %.

BEST MODE FOR CARRYING OUT THE INVENTION

The compound having the formula (III) as a starting compound can be prepared according to the process described in U.S. Pat. No. 4,968,814.

To be concrete, the compound (III) can be prepared by reacting an alkaline metal salt of 2-thiophenethiol with a 3-tosyloxybutyric acid ester.

Examples of the group represented by R in the formula (III) are, for instance, methyl group, ethyl group, n-propyl group, i-propyl group, n-butyl group, i-butyl group, sec-butyl group, tert-butyl group and the like. Among these, methyl group is preferable from the viewpoint that an alcohol or alcohol derivative produced during the reaction is easily removed by distillation.

Examples of the acid in the aqueous solution of acid to be used are, for instance, an inorganic acid such as hydrochloric acid, sulfuric acid or phosphoric acid; an organic acid such as trifluoroacetic acid, toluenesulfonic acid or methanesulfonic acid; and a Lewis acid such as boron trifluoride-diethyl ether complex or a boron fluoride. It is desirable to use hydrochloric acid or sulfuric acid because it is easy to industrially handle them in the waste disposal etc.

The concentration of the aqueous solution of acid to be used can be freely determined.

Examples of the organic solvent or the organic acid to be added are, for instance, an organic solvent such as dioxane, toluene, dichloromethane, chloroform, acetone or dimethoxyethane, and an organic acid such as acetic acid, formic acid, malonic acid, benzoic acid or tartaric acid which are a carboxylic acid. Particularly, when acetic acid or formic acid is used, good results are obtained.

The amount of the organic solvent or the organic acid, for example, carboxylic acid, to be added can be determined in an optional ratio to the amount of the compound (III). Particularly, when the amount is from 4 to 10 molar equivalents based on the compound (III), good results are obtained.

The compound having the formula (III) can be used for the reaction in an optional reaction concentration. When the reaction concentration thereof is from 5 to 30% by weight based on the total amount of the reaction mixture, good results are obtained.

A temperature during the reaction can be determined at an optional temperature of not more than the boiling point of the reaction mixture, and may be decided taking account of the acceptable reaction time.

In the case of carrying out the reaction as it is, the reaction reaches equilibrium in a conversion ratio which depends on the charging amount of the compound having the formula (III), the kind and amount of the acid in the aqueous solution of acid to be used, the amount of water used, and the kind and amount of the organic solvent or the organic acid to be added. However, it is possible to raise the conversion ratio up to any desired conversion ratio by removing a produced alcohol or alcohol derivative by distillation which has the formula (IV):

R—OX  (IV)

wherein R is a straight chain or branched $C_1$ to $C_4$ alkyl group and X is hydrogen atom or COR' wherein R' is hydrogen atom, a straight chain or branched $C_1$ to $C_3$ alkyl group or a phenyl group which may be substituted. Additionally, in the case that at this time, water is also removed by distillation together with the alcohol or alcohol derivative, water may be added to the reaction system in an amount of the removed water.

Examples of a group represented by R' in the formula (IV) are, for instance, hydrogen atom, methyl group, ethyl group, n-propyl group, i-propyl group, phenyl group, a toluyl group and the like.

The obtained 3-(2-thienylthio)butyric acid may be isolated and purified by a usual treating process such as solvent extraction, concentration or distillation, or may be used as it is.

The present invention is more specifically explained below by means of the Examples. However, it is to be understood that the present invention is not limited to those Examples.

REFERENCE EXAMPLE 1

There were mixed 180 g of a concentrated hydrochloric acid having a concentration of 35% and 146 g of water to prepare an aqueous solution of hydrochloric acid having a concentration of 5.8N.

The resulting aqueous solution of hydrochloric acid was mixed with 56 g of 3-(2-thienylthio)butyric acid methyl ester (net content 54 g), with stirring at room temperature. The mixture was warmed till the contents started to be refluxed and then was allowed to react under refluxing conditions for 23 hours. The progress of the reaction was monitored by means of a high-pressure liquid chromatography. The conversion ratio was 99 mol % and the amount of 3-(3-thienylthio) butyric acid produced was 0.82 mol % (mol % based on 3-(2-thienylthio)butyric acid).

The high-pressure liquid chromatography was carried out under the following conditions:

Column: Finepak SIL $C_{18-S}$ (4.6 mm×25 cm, made by JASCO CORP.)

Eluent: acetonitrile:water:phosphoric acid=4:6:0.006 (V/V)

Flow rate: 1.0 ml/min

Temperature: 40° C.

Detection condition: U.V. detector, wavelength: 230 nm 3-(2-Thienylthio)butyric acid $^1$H NMR (CDCl$_3$) 7.41 (M, 1 H), 7.17 (M, 1 H), 7.02 (M, 1 H), 3.37 (M, 1 H), 2.71 (dd, 1 H, J=16.0, J=6.4 Hz), 2.47 (dd, 1 H, J=16.0, J=8.0 Hz), 1.34 (d, 3 H, J=6.8 Hz)

$^{13}$C NMR (CDCl$_3$) 177.5 (s), 136.4 (s), 130.9 (s), 130.5 (s), 127.7 (s), 41.4 (s), 41.3 (s), 20.6 (s)

3-(3-Thienylthio)butyric acid $^1$NMR (CDCl$_3$) 7.35 (M, 2 H), 7.08 (M, 1 H), 3.45 (M, 1 H), 2.65 (dd, 1 H, J=15.6, J=6.4 Hz), 2.47 (dd, 1 H, J=15.6, J=8.4 Hz), 1.33 (d, 3 H, J=7.6 Hz)

$^{13}$NMR (CDCl$_3$) 177.6 (s), 132.2 (s), 129.1 (s), 128.3 (s), 126.2 (s), 41.6 (s), 39.6 (s), 20.9 (s)

EXAMPLE 1

There were mixed 13 g of a concentrated sulfuric acid having a concentration of 97% and 108 g of water to prepare an aqueous solution of sulfuric acid. To the resulting aqueous solution of sulfuric acid were added 90 g of acetic acid (6 molar equivalents based on 3-(2-thienylthio)butyric acid methyl ester) and 56 g of 3-(2-thienylthio)butyric acid methyl ester (net content 54 g), successively, and they were mixed. The mixture was allowed to react under refluxing for 24 hours. The progress of the reaction was monitored by means of a high-pressure liquid chromatography. The conversion ratio was 95 mol % and the amount of 3-(3-thienylthio)butyric acid produced was 0.01 mol % (mol % based on 3-(2-thienylthio)butyric acid).

The high-pressure liquid chromatography was carried out under the following conditions:

Column: Finepak SIL $C_{18-S}$ (4.6 mm×25 cm, made by JASCO CORP.)

Eluent: acetonitrile:water:phosphoric acid=4:6:0.006 (V/V)

Flow rate: 1.0 ml/min

Temperature: 40° C.

Detection condition: U.V. detector, wavelength: 230 nm

In order to further proceed the reaction, 11 g of the mixture of methyl acetate, methanol, acetic acid and water was removed by distillation and the remaining reaction mixture was allowed to react under refluxing for 7 hours. The conversion ratio was 99 mol % and the amount of 3-(3-thienylthio)butyric acid produced was 0.01 mol % (mol % based on 3-(2-thienylthio)butyric acid).

Each NMR data obtained as to 3-(2-thienylthio)butyric acid and 3-(3-thienylthio)butyric acid was consistent with that obtained in Reference Example 1.

EXAMPLES 2 TO 19

3-(2-Thienylthio)butyric acid was prepared in the same procedure as in Example 1 wherein the kind and amount of the acid in the aqueous solution of acid, the amount of water used, the kind and amount of the organic solvent or the organic acid to be added and the reaction time were changed. Whether the removal by distillation of the produced alcohol or alcohol derivative was done or not done is as shown in Table 1.

The results thereof are shown in Table 1.

TABLE 1

| Ex. No. | 3-(2-Thienylthio)-butyric acid methyl ester (net content) (g) | Organic solvent or organic acid Kind | Amount (g) | Equivalent (molar equivalent) | Acid in aqueous solution of acid Kind | Amount (g) | Amount of water used (g) | Reaction time (Hr) | Removal by distillation | Conversion ratio (mol %) | Amount of isomer produced (mol %) |
|---|---|---|---|---|---|---|---|---|---|---|---|
| 2 | 22 | Acetic acid | 36 | 10 | Hydrochloric acid | 26 | 285 | 32 | not done | 100 | 0.01 |
| 3 | 54 | Acetic acid | 150 | 10 | Sulfuric acid | 12 | 303 | 30 | done | 100 | 0.00 |
| 4 | 54 | Acetic acid | 90 | 6 | Sulfuric acid | 12 | 303 | 48 | done | 100 | 0.01 |
| 5 | 54 | Acetic acid | 90 | 6 | Sulfuric acid | 13 | 216 | 31 | done | 97 | 0.01 |
| 6 | 54 | Acetic acid | 60 | 4 | Sulfuric acid | 12 | 302 | 48 | done | 100 | 0.01 |
| 7 | 54 | Acetic acid | 90 | 6 | Sulfuric acid | 6 | 109 | 28 | done | 99 | 0.00 |
| 8 | 54 | Acetic acid | 90 | 6 | Sulfuric acid | 1.2 | 109 | 28 | done | 94 | 0.00 |
| 9 | 54 | Acetic acid | 90 | 6 | Sulfuric acid | 0.12 | 110 | 28 | not done | 40 | 0.00 |
| 10 | 54 | Acetic acid | 90 | 6 | Phosphoric acid | 8 | 108 | 48 | done | 96 | 0.00 |
| 11 | 54 | Formic acid | 123 | 10 | Sulfuric acid | 12 | 304 | 30 | done | 100 | 0.01 |
| 12 | 22 | Malonic acid | 63 | 6 | Sulfuric acid | 5 | 121 | 24 | done | 100 | 0.00 |
| 13 | 22 | Benzoic acid | 73 | 6 | Sulfuric acid | 5 | 121 | 72 | not done | 86 | 0.02 |
| 14 | 22 | Tartaric acid | 90 | 6 | Sulfuric acid | 5 | 121 | 28 | done | 82 | 0.02 |
| 15 | 54 | Acetic acid | 91 | 6 | Trifluoroacetic acid | 29 | 109 | 27 | done | 98 | 0.00 |
| 16 | 54 | Acetic acid | 90 | 6 | Toluenesulfonic acid *1 | 48 | 108 | 28 | done | 98 | 0.02 |
| 17 | 54 | Acetic acid | 90 | 6 | Methanesulfonic acid | 24 | 108 | 28 | done | 98 | 0.01 |
| 18 | 22 | Acetic acid | 36 | 6 | Boron trifluoride *2 | 14 | 44 | 26 | done | 98 | 0.01 |
| 19 | 54 | Dioxane | 90 | 4 | Sulfuric acid | 12 | 108 | 48 | not done | 81 | 0.00 |

*1; Toluenesulfonic acid monohydrate
*2; Boron trifluoride-diethyl ether complex

INDUSTRIAL APPLICABILITY

According to the present invention, 3-(2-thienylthio)butyric acid which is an important intermediate for a medicament used in the treatment of glaucoma MK-507, can be prepared with controlling the content of contamination by 3-(3-thienylthio)butyric acid, which is the position isomer, to at most 0.1 mol %.

We claim:

1. A process for preparing a compound having the structural formula

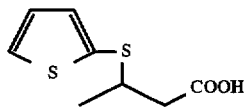   (I)

characterized by, in a reaction of a compound having the formula (III):

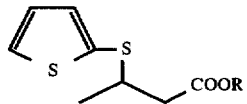   (III)

wherein R is a straight chain or branched $C_1$ to $C_4$ alkyl group, with an aqueous solution of acid, adding an organic solvent or an organic acid, removing by distillation an alcohol or alcohol derivative which is produced during the reaction and has the formula (IV):

R—OX   (IV)

wherein R is the same as defined above, and X is hydrogen atom or COR' where R' is hydrogen atom, a straight chain or branched $C_1$ or $C_s$ alkyl group or a phenyl group which may be substituted, whereby the production of a by-product compound having the structural formula (II):

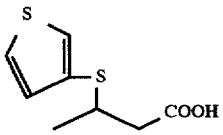   (II)

is controlled to at most 0.1 mol %.

2. The process of claim 1 wherein R in the formula (III) is methyl group.

3. The process of claim 1 or 2 wherein the organic solvent or the organic acid is a carboxylic acid.

4. The process of claim 3 wherein the carboxylic acid is acetic acid.

5. The process of claim 3 wherein the carboxylic acid is formic acid.

6. The process of claims 1, 2, 3, 4 or 5 wherein the acid in the aqueous solution of acid is hydrochloric acid, sulfuric acid, phosphoric acid, toluenesulfonic acid, methanesulfonic acid, trifluoroacetic acid or boron trifluoridie-diethyl ether complex.

7. The process of claim 6 wherein the acid in the aqueous solution of acid is hydrochloric acid.

8. The process of claim 6 wherein the acid in the aqueous solution of acid is sulfuric acid.

9. The process of claim 3 wherein an amount of the carboxylic acid to be added is from 4 to 10 molar equivalents based on the compound having the formula (III).

10. A process for preparing a compound having the structural formula (I):

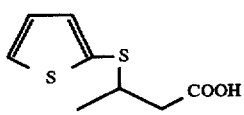 (I)

characterized by, in a reaction of a compound having the formula (III):

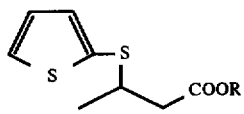 (III)

wherein R is a straight chain or branched $C_1$ to $C_4$ alkyl group, with an aqueous solution of sulfuric acid, adding an organic solvent or an organic acid, whereby the production of a by-product compound having the structural formula (II):

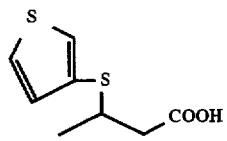 (II)

is controlled to at most 0.1 mol %.

11. A process for preparing a compound having the structural formula (I):

 (I)

characterized by, in a reaction of a compound having the formula (III):

 (III)

wherein R is a straight chain or branched $C_1$ to $C_4$ alkyl group, with an aqueous solution of acid, adding formic acid, whereby the production of a by-product compound having the structural formula (II):

 (II)

is controlled to at most 0.1 mol %.

* * * * *

UNITED STATES PATENT AND TRADEMARK OFFICE
CERTIFICATE OF CORRECTION

PATENT NO. : 5,723,628
DATED : March 3, 1998
INVENTOR(S) : KANOU et al

It is certified that error appears in the above-identified patent and that said Letters Patent is hereby corrected as shown below:

In column 6, on line 37, please change "$C_1$ or $C_s$" to be --$C_1$ or $C_3$-- therefor.

Signed and Sealed this

Fourteenth Day of December, 1999

Attest:

Q. TODD DICKINSON

Attesting Officer

Acting Commissioner of Patents and Trademarks